US006846923B2

(12) United States Patent
Wang et al.

(10) Patent No.: US 6,846,923 B2
(45) Date of Patent: Jan. 25, 2005

(54) OXIME-LINKED POLYSACCHARIDES AND METHODS OF PREPARING THE SAME

(75) Inventors: Peng George Wang, Troy, MI (US); Wenhua Xie, Westland, MI (US); Lei Qiao, Downingtown, PA (US); Huai N. Cheng, Wilmington, DE (US); Dennis J. Murphy, Malvern, PA (US); Qu-Ming Gu, Hockessin, DE (US)

(73) Assignee: Hercules, Inc., Wilmington, DE (US)

( * ) Notice: Subject to any disclaimer, the term of this patent is extended or adjusted under 35 U.S.C. 154(b) by 87 days.

(21) Appl. No.: 09/956,742

(22) Filed: Sep. 18, 2001

(65) Prior Publication Data

US 2003/0060446 A1 Mar. 27, 2003

(51) Int. Cl.⁷ .............................. C07H 5/04; C07H 5/06; C08B 37/00
(52) U.S. Cl. .................... 536/55.1; 536/18.7; 536/55.2; 536/114; 536/123.1; 536/126
(58) Field of Search ............................... 536/18.7, 55.1, 536/55.2, 114, 123.1, 126

(56) References Cited

U.S. PATENT DOCUMENTS

| | | | |
|---|---|---|---|
| 5,514,379 A | 5/1996 | Weissleder et al. | 424/426 |
| 5,543,058 A | 8/1996 | Miller | 210/725 |
| 5,554,745 A | 9/1996 | Chiu et al. | 536/52 |
| 5,575,840 A | 11/1996 | Dewacker | 106/162.81 |
| 5,928,474 A | 7/1999 | Moffett | 162/168.3 |
| 6,025,311 A | 2/2000 | Clarke et al. | 510/121 |
| 6,093,769 A | 7/2000 | Burdick et al. | 524/767 |
| 6,113,891 A | 9/2000 | Burdick et al. | 424/70.13 |
| 6,303,585 B1 | 10/2001 | Spiro et al. | 514/54 |

FOREIGN PATENT DOCUMENTS

WO    WO 99/01143    1/1999

OTHER PUBLICATIONS

Andreana et al. Organic Letters (2002), vol. 4, pp. 1863–1866.*
Rodriguez et al. J. Org. Chem. (1998), vol. 63, pp. 7134–7135.*

Canne,L.E. et al., "Total chemical synthesis of a unique transcription factor–related protein",*J. Am. Chem. Soc.* 1995, 117, 2998–3007.

Cao, S. et al., "Steroselective phase transfer catalyzed synthesis of glycosyloxysuccinimides and their transformations into glycoprobes", *Tetrahedron*, 1995, 51, 6679–6686.

Cervigni, S.E. et al., "Synthesis of glycopeptides and lipopeptides by chemoselective ligation",*Agnew. Chem. Int. Ed.* 1996, 35, 1230–1232.

Liu,C.F. et al., "Orthogonal ligation of unprotected peptide segments through pseudoproline formation for the synthesis of HIV–1 protease analogs" *J. Am. Chem. Soc.* 1996, 118, 307–312.

Liu, C.F., et al., "Sugar–containing polyamines prepared using galactose oxidase coupled with chemical reduction", *J. Amer. Chem. Soc.*, 1999, 121, 466–467.

Lu, W. et al., "Comparative total synthesis of turkey ovomucoid third domain by both stepwise solid phase peptide synthesis and native chemical ligation" *J. Am. Chem. Soc.* 1996, 118, 8518–8523.

Rodriquez,E.C. et al., "A strategy for the chemoselective synthesis of O–linked glycopeptides with native sugar–peptide linkages", *J. Am. Chem. Soc.* 1997, 119, 9905–9906.

Tressel,P.S., et al., "Galactose oxidase from dactylium dendroides", *Methods in Enzymology*, 1982, 89, 163–171.

Zhao, Y. et al., "Rapid, sensitive structure analysis of oligosaccharides", *Proc. Natl. Acad. Sci. U.S.A.* 1997, 94, 1629–1633.

* cited by examiner

*Primary Examiner*—James O. Wilson
*Assistant Examiner*—Patrick Lewis
(74) *Attorney, Agent, or Firm*—Woodcock Washburn LLP

(57) ABSTRACT

Polysaccharides comprising one or more oxime linkages are provided. Methods for their preparation include the polycondensation of saccharides bearing oxime-forming substituents. In some embodiments, polymerization is conducted in the presence of galactose oxidase. The resulting oxime-linked polysaccharides have desirable properties and are useful in numerous applications including paper manufacturing and drug delivery vehicles.

40 Claims, 3 Drawing Sheets

OXIME-LINKED POLYSACCHARIDES AND METHODS OF PREPARING THE SAME

FIELD OF THE INVENTION

The present invention relates to novel polysaccharides. More particularly, the present invention relates to oxime-linked polysaccharides and methods for their preparation.

BACKGROUND OF THE INVENTION

Polysaccharides are highly prevalent in plants and animals, and frequently have important roles in biological structure. Both natural and synthetic polysaccharides may be useful in a wide variety of commercial applications including, for example, in paper products, foodstuffs, hydrogels, thickeners, water treatment applications, encapsulating media, drug delivery, hair treatment, wound healing, skin care, etc., to name a few. Most naturally occurring polysaccharides are built from sugar-based molecules that are connected through glycosidic linkages. Synthetic polysaccharides containing unnatural linkages may also be useful, thereby expanding the role of polysaccharides in both industrial applications and commercial products.

Unnatural linkages may be advantageous in polysaccharides as their incorporation may serve to mediate polymer properties. For example, unnatural linkages may affect crystallinity or solubility in a predictable fashion. Unnatural linkages may also allow for the introduction of derivatizable functionalities in polysaccharides. For example, nitrogen-containing polymers may be readily derivatized by chemical transformations, such as reduction, oxidation, protonation, etc. of the nitrogen-containing functionalities, leading to changes in both electronic and structural features of the polymer. Despite the versatility and potential for nitrogen-containing polymers, polysaccharides having nitrogen functionalities in the polymer backbone are rare and represent a relatively undeveloped field of polymer chemistry.

Methods for polysaccharide synthesis that incorporate unnatural linkages may also facilitate control over the saccharide composition of the polysaccharide product. For instance, unnatural linkages may allow preparation of polysaccharides by assembly of either or both monomeric and oligomeric building blocks. The ability to synthesize new polysaccharides by piecing together monosaccharides, disaccharides, trisaccharides, and/or low molecular weight polysaccharides may lead to greater control over polymer properties and open the door for the synthesis of new materials with mixed linkages.

Whereas a number of strategies for polysaccharide synthesis involving unnatural linkages are known (e.g., Hanessian in, *Preparative Carbohydrate Chemistry*, Dekker, New York, 1996; and Khan and O'Neill, eds., *Modern Methods in Carbohydrate Synthesis*, Harwood, Amsterdam, 1996), most of these methods lead to low molecular weight polysaccharides. An exception is a recent work that reports chemoenzymatic synthesis of sugar-containing polymers (Liu, et al., *J. Amer. Chem. Soc.*, 1999, 121, 466). In this article, galactose oxidase is used first to selectively oxidize the −6 on galactose to an aldehyde group. Subsequently, polycondensation of the aldehyde group with an aminosugar via reductive amination affords amine-linked polysaccharides. However, the reported isolated yields in these reactions are relatively low (7–20%), most likely due to the formation of a large amount of low molecular weight oligomeric products.

Presently, among the many methods developed for the synthesis of polysaccharides, the condensation of ketones and aldehydes with aminooxy groups has not been reported as being employed in polymerization reactions. This oxime-forming reaction, however, is well known outside the realm of polymer chemistry (See, e.g., Canne, et al., *J. Am. Chem. Soc.* 1995, 117, 2998; Lu, et al., *J. Am. Chem. Soc.* 1996, 118, 8518;. Liu, et al., *J. Am. Chem. Soc.* 1996, 118, 307; Rodriguez, et al., *J. Am. Chem. Soc.* 1997, 119, 9905; Cervigni, et al., *Angew. Chem. Int. Ed.* 1996, 35, 1230; Zhao, et al., *Proc. Natl. Acad. Sci. U.S.A.* 1997, 94, 1629).

Polysaccharides are versatile and desirable polymers as indicated by their prevalence in numerous industrial applications and commercial embodiments. New polysaccharides may be needed to satisfy the ever-increasing demand for improved materials. The importance of polysaccharides in applications related to, for example, water treatment, paper products, hydrogel wound care, encapsulation, drug delivery, skin care, etc. clearly shows a need for polysaccharides that are stable, non-toxic, amenable to aqueous systems and biocompatible. The large-scale use of polysaccharides also creates a need for their efficient preparation from inexpensive starting materials in environmentally safe solvent systems such as water. Preparative methods involving assembly of different saccharides such as mono-, di-, tri-, and low molecular weight polysaccharides are also desirable and may lead to new polysaccharides having novel compositions and properties. The oxime-linked polysaccharides and their methods of preparation described herein can help fulfill these and other needs.

SUMMARY OF THE INVENTION

The present invention is directed, in part, to improved polysaccharides containing at least one oxime linkage. Specifically, in one aspect, there are provided polysaccharides of Formula I:

I wherein:
A is, independently, a monosaccharide, disaccharide, trisaccharide, or low molecular weight polysaccharide residue; and
n is about 4 to about 10,000.

Another aspect of the invention relates to processes for preparing a polysaccharide comprising at least one oxime linkage, the process comprising contacting a first saccharide with a second saccharide in the presence of galactose oxidase, wherein each of the saccharides comprises at least one —$ONH_2$ functionality and at least one —$CH_2OH$ functionality oxidizable by the galactose oxidase.

Still another aspect of the invention relates to processes of preparing a polysaccharide comprising at least one oxime linkage, the process comprising contacting a first saccharide with a second saccharide, wherein each of the saccharides comprises at least one —$ONH_2$ functionality and at least one precursor to a —CHO functionality, and converting the precursor to the —CHO functionality.

Yet another aspect of the invention relates to processes of preparing a polysaccharide comprising at least one oxime linkage, the process comprising contacting a first saccharide with a second saccharide, wherein each of the saccharides comprises at least one —CHO functionality and at least one —$ONH_2$ functionality.

These and other aspects of the invention will become more apparent from the present specification and claims.

BRIEF DESCRIPTION OF THE DRAWINGS

For the purpose of illustrating embodiments of the invention, there are shown in the drawings forms which are presently preferred. It should be understood, however, that this invention is not limited to the precise arrangements and instrumentalities shown.

DETAILED DESCRIPTION OF PREFERRED EMBODIMENTS

Figure 1:
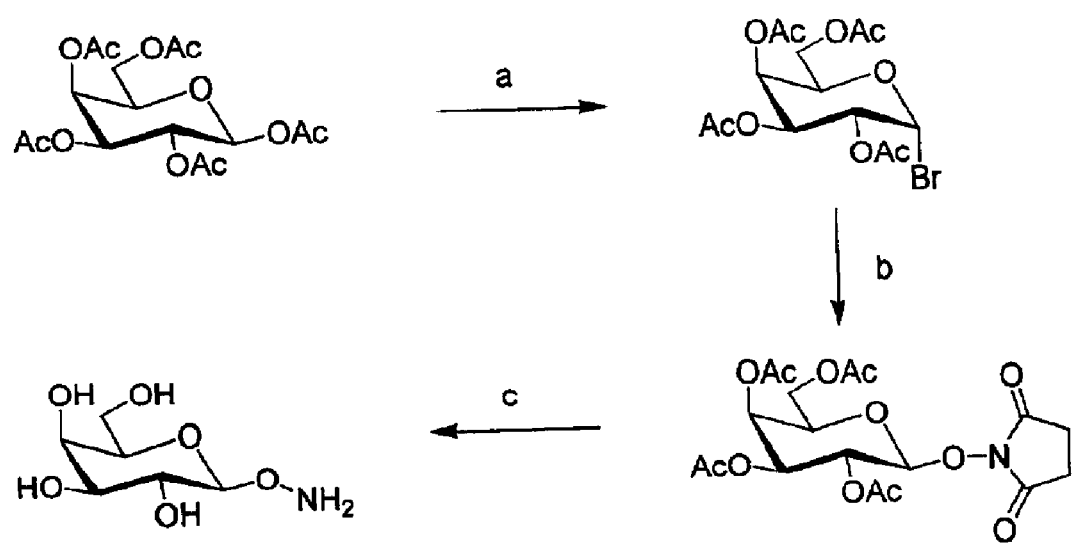
FIG. 1 includes a schematic depiction of the synthesis of a monosaccharide for use in the preparation of a polysaccharide in accordance with an embodiment of the present invention.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

The term "polysaccharide," as used herein, refers to a polymer comprising a plurality (i.e., two or more) of covalently linked saccharide residues. Linkages may be natural or unnatural. Natural linkages include, for example, glycosidic bonds, while unnatural linkages may include, for example, ester, amide, or oxime linking moieties. Polysaccharides may have any of a wide range of weight average molecular weight ($M_w$) values of at least about 500 daltons. For example, the polysaccharides can have molecular weights of at least about 1000, 2000, 4000, 6000, 8000, 10,000 daltons or even higher. Polysaccharide may have straight chain or branched structures. The phrase "low molecular weight polysaccharide," as used herein, is meant to refer to a polysaccharide having a weight average molecular weight ranging from about 500 to about 5000 daltons, or more preferably from about 500 to about 2000 daltons, or even more preferably from about 500 to about 1000 daltons. Low molecular weight polysaccharides can be generated by degradation (e.g., hydrolysis) of larger polysaccharides. Degradation can be achieved by any of a variety of means known to those skilled in the art including treatment of polysaccharides with acid, base, heat, or enzymes to yield degraded polysaccharides. Enzymatic degradation of galactomannan gums using mannanase is well known to those skilled in the art as a process that yields, inter alia, degraded galactomannan gums comprising low molecular weight polysaccharides.

As used herein, the phrase "oxime-linked polysaccharides" are polysaccharides containing at least one oxime linkage, preferably at least two oxime linkages, and even more preferably at least three oxime linkages. If desired, the oxime-linked polysaccharides may contain up to about 10,000 oxime linkages, or an even greater number.

As used herein, the term "saccharide" or "saccharide molecule" refers generally to any molecule typically understood by one skilled in the art to be a member of the sugar family of molecules, including, for example, aldoses and ketoses. Saccharides are the building blocks of polysaccharides. Saccharides may be in their straight-chain or cyclic hemiacetal forms. The saccharides may be naturally occurring or synthetic, and include all of the corresponding stereoisomers. Saccharides include monosaccharides, disaccharides, trisaccharides, low molecular weight polysaccharides, and derivatives thereof, including for example saccharides having substituents, side chains, or functionalizations that impart desired properties or reactivity. A "saccharide residue" is derived from a saccharide and represents the saccharide after incorporation into a polysaccharide. In referring to saccharide residues of oxime-linked polysaccharides, it is generally meant that the residues do not include the atoms of attached oxime linkages (—CH=N—O—) even though the atoms of the oxime linkage may originate from the saccharide molecules themselves.

The term "precursor," as used herein, refers to a chemical group or moiety that may be chemically converted to another group or moiety. For example, a primary alcohol group may be oxidized to an aldehyde group and therefore may serve as a precursor to an aldehyde. Other precursors to aldehydes include protected aldehydes.

The term "contacting" as used herein, means the bringing together or combining of molecules such that they are within a distance which allows for intermolecular interactions and chemical transformations. Contacting preferably occurs in solution phase in which the combined or contacted molecules are dissolved in a common solvent and are allowed to freely associate.

The present invention encompasses, inter alia, oxime-linked polysaccharides. These synthetic polymers preferably comprise a plurality of saccharide residues covalently connected through one or more oxime linkages (—CH=N—O—). Other types of linkages may also be present in the polysaccharides and may include both natural and unnatural linkages. The oxime linkages tend to be stable in water and may be readily formed in aqueous solvent. These properties may facilitate the preparation of the present oxime-linked polysaccharides, and may also indicate the advantageous and desirable stability of the present polymers in a wide range of practical applications. In addition, the present oxime-linked polysaccharides may have a weight average molecular weight ($M_w$) of at least about 1000 daltons, but higher values may be preferred because of the generally wider range of industrial applications for polymers of higher molecular weight. Thus, polysaccharides of at least about 2000, 4000, 6000, 8000, 10,000 daltons or higher may be preferred polysaccharides.

Oxime linkages of the present polysaccharides may be formed through a coupling reaction between saccharides having oxime-forming substituents. Each saccharide involved in the formation of oxime linkages preferably comprises at least one of two different functional groups, designated X and Y for example, that may form a linking oxime moiety when one saccharide molecule comprising X is contacted with another saccharide molecule comprising Y. In this way, a plurality of saccharides may be polymerized by the coupling of X and Y functionalities. Suitable oxime-forming X and Y pairs include aminooxy (—ONH$_2$) and aldehyde (—CHO) groups, or groups that can be chemically or enzymatically converted to aminooxy and aldehyde groups. The reaction of aminooxy groups with aldehyde groups to form oximes, which is generally spontaneous, is well known to those skilled in the art of synthetic organic chemistry.

In preferred embodiments, the polysaccharides of the present invention have the following Formula I:

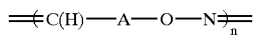

wherein A is, independently, a saccharide residue such as a monosaccharide, disaccharide, trisaccharide, or low molecular weight polysaccharide residue; and n is about 4 to about 10,000. The residues represented by A correspond to saccharides after incorporation into the polysaccharide and do not include atoms involved in the oxime linkages such as, for example, the C, N, and O atoms represented in Formula I above. For example, if residue A is derived from a galactose monosaccharide shown in Formula II, A may represent the galactose residue shown in Formula III.

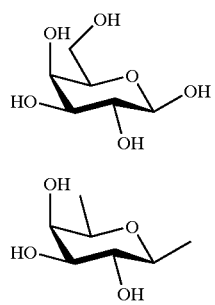

As indicated in Formula I, the C and O atoms of the oxime linkage may connect to any atom of residue A. In preferred embodiments, the C atom of the oxime linkage may be derived from a primary alcohol moiety of the saccharide involved in oxime formation. For instance, when the saccharide residue is derived from galactose, the C atom of the oxime group may correspond to the C-6 atom. Similarly, the O atom of the oxime group may be preferably derived from an aminooxy (—ONH$_2$) moiety attached to any atom of the saccharide that is involved in oxime formation. For example, in embodiments when the saccharide residue is derived from galactose, the aminooxy group is preferably attached to C-1.

Further, saccharides involved in forming oxime linkages preferably comprise, or may be derivatized to bear, at least one aminooxy or aldehyde group. In preferred embodiments, each of the saccharides preferably comprises at least one aminooxy group and at least one aldehyde group, so that a plurality of saccharides may be polymerized. Saccharide molecules may also bear groups that can be chemically or enzymatically converted to aminooxy and/or aldehyde groups. For instance, in some embodiments, a preferred functionality is a primary alcohol that may be converted by oxidation to an aldehyde. The conversion may be chemical or enzymatic, such as in the enzymatic oxidation of galactose by the enzyme galactose oxidase (GO). This enzyme generally catalyzes oxidation of the C-6 of galactose specifically or of other similar substrates with the C-6 galactose configuration, thereby converting the primary alcohol to an aldehyde group. Galactose oxidase may be obtained by a wide variety of manners, e.g., by fermenting various wild type and cloned fungi, but is typically obtained from Fusarium spp (NRRL 2903). Cultures may also be obtained from the American Type Culture Collection under Dactylium dendroides ATCC 46032 and they may be successfully fermented under the procedure of Tressel, et al., *Methods in Enzymology*, 1982, 89, 163. Use of galactose oxidase to oxidize saccharides is well known to those skilled in the art, as the enzyme has been used extensively in paper manufacturing as described, for example, in U.S. Pat. No. 5,554,745, the disclosure of which is incorporated herein by reference in its entirety.

Saccharide residues may be derived from any saccharide or derivative thereof which would be apparent to one of ordinary skill in the art, once armed with the teachings of the present disclosure. Saccharides that may lend well to functionalization and polymerization according to the methods of preparing oxime-linked polysaccharides provided herein are preferred. In preferred form, the saccharides may be substrates of the enzyme galactose oxidase. For example, preferred monosaccharides include, for example galactose or galactose derivatives, especially D-galactose. Preferred disaccharides include, for example, lactose, melibiose, galactosyl arabinose, and derivatives thereof. Preferred low molecular weight polysaccharides may comprise terminal or pendant saccharide moieties, such as galactose moieties, capable of being oxidized by galactose oxidase. As such, preferred low molecular weight polysaccharides include degraded galactomannan gums or their ether derivatives, arabinogalactan gums or their ether derivatives, galactoglucomannan hemicelluloses or their ether derivatives. Preferred galactomannan gums include, for example, guar, locust bean, tara, fenugreek and the like. Preferred arabinogalactan gums include, for example, arabic, larch, tragacanth gums, and the like. Other saccharide substrates of galactose oxidase include raffinose, methyl-alpha-D-galactopyranose, and methyl-beta-D-galactopyranose and may also be suitable for preparing the oxime-linked polysaccharides of the present invention. Other substrates of galactose oxidase include dihydroxyacetone and glycerol. Saccharides bearing substituents derived from dihydroxyacetone or glycerol may also be suitable for preparing the present polysaccharides.

The present invention further encompasses processes for the preparation of oxime-linked polysaccharides. In a preferred embodiment, the processes comprise the steps of contacting a first saccharide with a second saccharide, wherein the first and second saccharides may be the same or different, in the presence of galactose oxidase. Each of the saccharides preferably comprises at least one primary alcohol functionality (—CH$_2$OH) capable of being oxidized by galactose oxidase and at least one aminooxy functionality (—ONH$_2$). By themselves, the alcohol and aminooxy functionalities when combined or contacted are generally not significantly reactive with one another. Not wishing to be bound by any theory or theories of operation, however, it is believed that in the presence of galactose oxidase, the —CH$_2$OH group is enzymatically converted in situ to an aldehyde (—CHO) which then reacts with the aminooxy group to form a linking oxime.

As mentioned previously, it is well known that the enzyme galactose oxidase may catalyze a reaction in which a primary alcohol such as the C-6 hydroxyl group of galactose is oxidized to an aldehyde. This reaction occurs with concomitant reduction of molecular oxygen to hydrogen peroxide. Preferably the oxidation with galactose oxidase may be carried out in the presence of a means to consume, decompose or otherwise remove the hydrogen peroxide by-product. For example, in preferred embodiments, hydrogen peroxide may be enzymatically decomposed using a catalase. Other metal complexes and compounds can also be used to decompose the hydrogen peroxide formed in the oxidation reaction. Chemicals that will accomplish redox chemistry with hydrogen peroxide are iron complexes, e.g., with polyamines (notably triethylenetetramine) and persulfates.

Saccharides comprising at least one aminooxy functionality, for preparing the polysaccharides of the present invention, may be readily prepared by one skilled in the art. For instance, the conversion of saccharides (including, for example, monosaccharides, disaccharides, trisaccharides, and low molecular weight polysaccharides) to their respective 1-O-hydroxylamino derivatives has been previously reported. Key steps include the formation of an N-hydroxylsuccinimidoglycoside followed by cleavage of the succinamide group with hydrazine to yield the desired saccharide with an aminooxy functionality (Cao, et al., *Tetrahedron*, 1995, 51, 6679, which is incorporated herein by reference in its entirety). For illustration, a schematic for the synthesis of 1-O-hydroxylamino galactose is provided in FIG. 1 where reagents are (a) HBr/HOAc; (b) N-hydroxyl succinamide and 1:1 $CH_2Cl_2$/1M $Na_2CO_3$; and (c) $N_2H_4$—$H_2O$. The 1-O-hydroxylamino derivatives of other saccharides may be prepared similarly.

Figure 2:
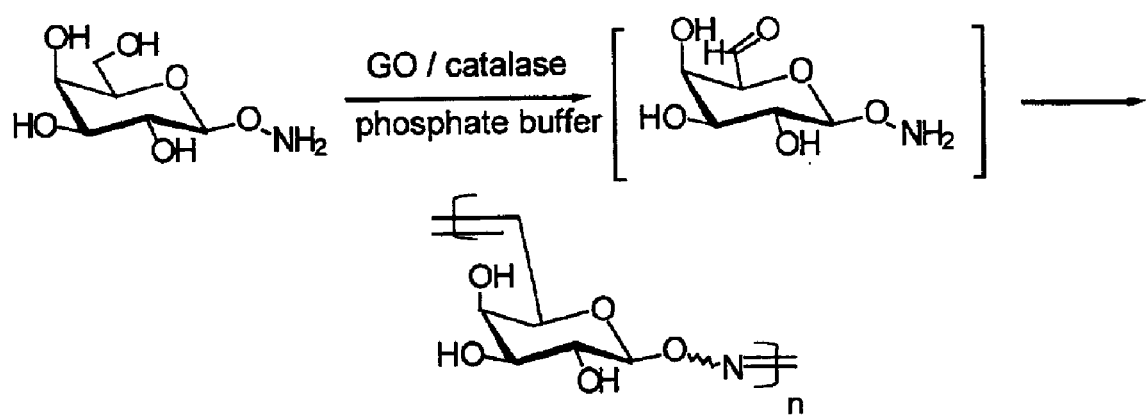
FIG. 2 includes a schematic depiction of a preferred polysaccharide in accordance with an embodiment of the present invention.
Figure 3:
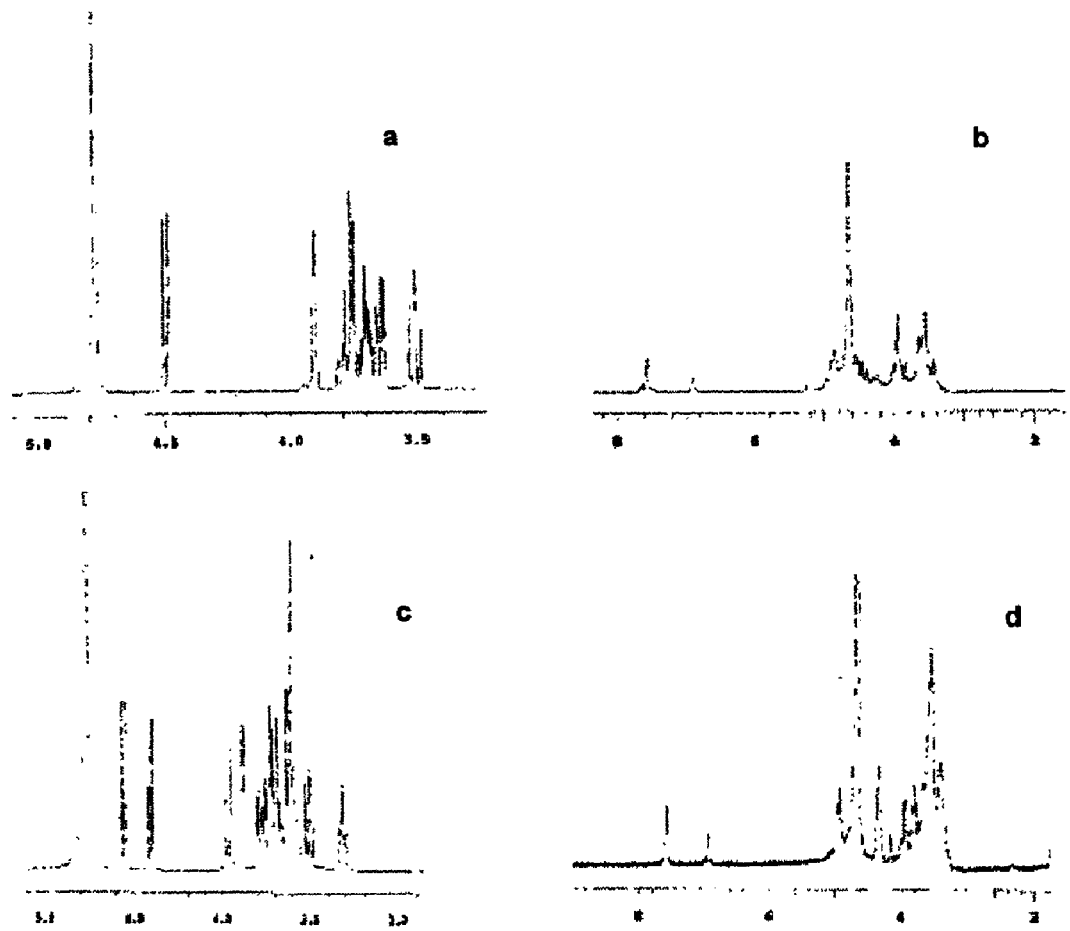
FIGS. 3a–3d include NMR spectra of starting material and polysaccharides in accordance with an embodiment of the present invention.

Polymerization resulting in the formation of oxime-linked polysaccharides of the present invention may preferably be achieved by galactose oxidase catalyzed oxidation of saccharide molecules having both aminooxy (e.g., 1-O-hydroxylamino) and primary hydroxyl groups (e.g., C-6 primary alcohol). An example of this reaction is provided in FIG. 2 for 1-O-hydroxylamino galactose. This reaction may advantageously proceed readily at room temperature with formation of oxime-linked polysaccharides. 1-O-hydroxylamino derivatives of disaccharides behave similarly, although polymerization may be relatively slower.

In an alternative process for the preparation of oxime-linked polysaccharides, first and second saccharides are combined or contacted with each other, where each of the saccharide molecules preferably comprises at least one aldehyde group (—CHO) and at least one aminooxy group (—$ONH_2$) that may react together to form an oxime linkage. Either functionality may comprise a protecting group, or be in protected form when contacted, to facilitate manipulations. Removal of the protecting group may allow initiation of the polymerization reaction. Protecting groups for amino and aldehyde functionalities are well known to those skilled in the art (see, e.g., Greene, et al, *Protective Groups in Organic Synthesis*, second ed., John Wiley & Sons, New York, 1991). For instance, an aldehyde may be readily protected as an acetal or hemiacetal that is generally unreactive toward an aminooxy group. Conversion of the acetal or hemiacetal moiety to an aldehyde moiety may initiate polymerization.

In preferred form, the oxime-containing polysaccharides of the present invention are water-soluble and non-crystalline and may be used as an additive in aqueous solutions or polymer compositions. In addition, one or more of the oxime linkages may be further modified; for example, the polymer may be hydrogenated to convert one or more of the oxime linkages to aminooxy linkages. The nitrogen in the polymer may also be derivatized to give a cationic charge. Thus, the present polysaccharides and derivatives thereof may be used, for example, as flocculants, or in flocculating media for the purification of water or liquids. Flocculants and their use in the treatment of wastewater are described, for example, in U.S. Pat. No. 5,543,058, which is incorporated herein by reference in its entirety. The present polysaccharides may also be used as retention aids in polymer compositions, especially paper pulp compositions. Use of polysaccharides or similar polymers as retention aids is described, for example, in U.S. Pat. Nos. 5,575,840 and 5,928,474, each of which is incorporated herein by reference in its entirety. In addition, the present oxime-linked polysaccharides may be useful in personal care products such as shampoos, moisturizers, sunscreens, cosmetics, and the like. Use of polysaccharides in personal care formulations is described, for example, in U.S. Pat. Nos. 6,113,891; 6,093,769; and 6,025,311, each of which is incorporated herein by reference in its entirety. The present polysaccharides may be particularly useful in hydrogels which are highly hydrated self-supporting films that may be suitable for use as coverings and protection materials for cutaneous lesions and/or pathologies. Consequently, hydrogels are often used in personal care formulations such as wound care products for topically applying pharmaceuticals because they may be adaptable to the lesion surface without strongly adhering to it, and may be permeable to gas but impermeable to liquids and bacteria. Use of polysaccharides in hydrogel formulations is provided, for example, in U.S. Pat. No. 5,514,379, which is incorporated herein by reference in its entirety. The present polymers may also be suitable for incorporating into drug delivery vehicles for the measured release of therapeutic agents, such as in drug encapsulants; for the encapsulation of biomedical devices for implantation (to increase the stability and biocompatibility of the devices); for the preparation of materials which prevent adhesion; for the preparation of bioadhesives; for the preparation of dressings useful in wound healing; and the like. These and other uses of the compounds of the present invention will be readily apparent to one of skill in the art, once armed with the present disclosures.

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention.

The following Examples are actual.

EXAMPLES

The invention is further demonstrated in the following examples. All of the examples are actual examples. The examples are for purposes of illustration and are not intended to limit the scope of the present invention.

Example 1

Formation of 1-O-Hydroxylamino-galactose

Pentaacetyl galactose (D-galactose pentaacetate) (5 g) was dissolved with stirring in 15 ml of HBr—HOAc (32%, w/w). After 6 hours of stirring, the resulting mixture was diluted with $CH_2Cl_2$ (120 ml) and poured into crushed ice in saturated $NaHCO_3$ solution (300 ml). The organic phase was separated and washed again with ice-cooled saturated $NaHCO_3$ solution (150 ml) in a separatory funnel. The organic phase was dried over anhydrous $Na_2SO_4$ and evaporated to dryness to give 4.8 g (yield, 91%) of the bromide. The bromide was redissolved in $CH_2Cl_2$ (15 ml) and stirred vigorously with 1 M $Na_2CO_3$ solution (15 ml) containing N-hydroxyl succinimide (5.0 g), tetrabutyl hydrogensulfate (5.0 g) for 4 hours. $CH_2Cl_2$ (80 ml) was then added. The organic phase was washed with water (2×30 ml) and dried with anhydrous $Na_2SO4$. Column chromatography (ethyl acetate/hexanes: 2.5/1) afforded 4.25 g (yield, 81%) of the N-succinimido compound.

The N-succinimido compound (2.0 g) was dissolved in 150 ml of methanol. Hydrazine (3 ml) was added, and the resulting mixture was stirred for 12 hours. After removal of volatiles in vacuo, the residue was dissolved in a minimum amount of water and subjected to gel filtration (Sephadex G-25), which gave 0.60 g of pure 1-O-hydroxylamino-galactose (yield, 68%).

Example 2
GO Reaction and Polymerization of 1-O-Hydroxyamino-galactose

A mixture of 200 mg 1-O-hydroxylamino-galactose, 120 unit of GO and 1200 unit of catalase in 10 ml phosphate buffer (50 mM. pH=7.0) containing 3 mg of $CuSO_4 \cdot 5H_2O$ was stirred gently with air bubbling through an air pump. After 10 hours, the starting material was entirely consumed as indicated by TLC. The reaction mixture was heated at 100° C. for 5 minutes to denature the enzyme. After filtration, the filtrate was dialyzed (using a dialysis membrane with molecular weight cutoff of 1000 daltons). Lyophilization of the retentate gave a whitish solid (yield 62%)

Example 3
GO-mediated Polymerization of Different 1-Hydroxyamino Sugars

The procedures outlined in Examples 1 and 2 have been repeated for galactose and several disaccharides. The results are summarized in Table 1. The reactions of 1-O-hydroxylamino-galactose proceeded readily at room temperature. The corresponding reactions for 1-O-hydroxylamino derivatives of disaccharides were found to be slower under the same conditions. Nevertheless, polymerization did take place in both cases.

In order to monitor the reactions, thin layer chromatography (TLC) was used. As the reaction proceeded, a spot began to show at the bottom of the silica-gel TLC plate (the solvent system being i-PrOH/$H_2O$/$NH_3$—$H_2O$ at 7:3:2). The spot did not move even with more polar solvent systems. FIGS. 3a–3d show the $^1H$ NMR spectra of the products isolated from the reactions of galactose and lactose. Specifically, spectra corresponding to starting material and polymer product are as follows: (3a) 1-$OHN_2$ galactose; (3b) gal-polymer; (3c) 1-$OHN_2$ lactose; and (3d) lac-polymer. The spectra of the products show remarkable differences from those of the starting monomers. In addition to totally different display patterns, all the lines are considerably broadened. The two signals in the region from 6.90–8.00 ppm belong to the proton on the oxime carbon, which exists in cis and trans configurations on the polymer chains.

The molecular weights of the polymers were determined by size exclusion chromatography (SEC) using dextran standards. The polymers have $M_w$ in the range of 4000–9000 daltons. The polydispersity is narrow, around 2.0.

TABLE 1

GO-mediated polymerization of 1-O-hydroxylamino sugars

| Reaction # | Monomer | $M_w$ | $M_w/M_n$ |
|---|---|---|---|
| 2[a] | 1-$ONH_2$ Gal | 4000 | 1.7 |
| 3[a] | 1-$ONH_2$ Lac | 7800 | 1.9 |
| 4[a] | 1-$ONH_2$ Melibiose | 4500 | 2.3 |
| 5[a] | 1-$ONH_2$-Gal-Ara | 7300 | 2.4 |
| 6[b] | 1-$ONH_2$ Gal | 4200 | 1.9 |
| 7[b] | 1-$ONH_2$ Lac | 7500 | 1.8 |
| 8[c] | 1-$ONH_2$ Gal | 5100 | 2.0 |
| 9[c] | 1-$ONH_2$ Lac | 8900 | 2.1 |

[a]In phosphate buffer (50 mM, pH = 7.0);
[b]In phosphate buffer (50 mM, pH = 5.5);
[c]Polymers from the reaction involving phosphate buffer (50 mM, pH = 7.0) were stirred in 0.2 M acetic acid for 24 hr. Abbreviations: Gal = galactose, Lac = lactose, and Ara = arabinose.

As shown in Table 1, polymers resulting from the polymerization of 1-O-hydroxylamino-galactose and 1-O-hydroxylamino-lactose in phosphate buffer at pH=7.0 had weight-average molecular weights ($M_w$) of 4,000 and 7,800, respectively (reactions 2 and 3). For reactions in phosphate buffer at pH=5.5 (reactions 6 and 7), almost the same molecular weights were obtained. In another experiment, the resulting polymers were stirred in an acidic solution (0.2 M HOAc) for a longer period of time (24 hours) (reactions 8 and 9). The molecular weights obtained in this experiment were slightly higher than in corresponding reactions 6 and 7.

To show that disaccharides, trisaccharides, and low molecular weight polysaccharides with pendant or terminal galactose groups should also produce oxime-linked polysaccharides, two examples of disaccharides (reactions 4 and 5) were performed, since it is well known that GO catalyzes the selective oxidation of the C-6 of the terminal galactose moiety in a variety of structures. The results are also shown in Table 1. The extension to other low molecular weight polysaccharides, e.g., degraded guar and locust bean gums, is straightforward.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed is:

1. A polysaccharide of Formula I:

wherein:
A is, independently, a monosaccharide, disaccharide, trisaccharide, or low molecular weight polysaccharide residue; and
n is about 4 to about 10,000.

2. A polysaccharide of claim 1 wherein said monosaccharide residue is derived from galactose.

3. A polysaccharide of claim 1 wherein said disaccharide residue is derived from lactose, melibiose, or galactosyl arabinose.

4. A polysaccharide of claim 1 wherein said low molecular weight polysaccharide residue is derived from degraded galactomannan gum.

5. A polysaccharide of claim 4 wherein said degraded galactomannan gum comprises guar, tara, fenugreek, or locust bean gum.

6. A polysaccharide of claim 1 wherein said low molecular weight polysaccharide has a $M_w$ of from about 500 to about 5000 daltons.

7. A polysaccharide comprising at least one oxime linkage and having a weight average molecular weight of at least about 1000 daltons.

8. A polysaccharide of claim 7 having a weight average molecular weight of at least about 4000 daltons.

9. A polysaccharide of claim 7 which comprises a plurality of saccharide residues selected from the group consisting of monosaccharide, disaccharide, trisaccharide, and low molecular weight polysaccharide residues.

10. A polysaccharide of claim 9 wherein said monosaccharide residue is derived from galactose.

11. A polysaccharide of claim 9 wherein said disaccharide residue is derived from lactose, melibiose, or galactosyl arabinose.

12. A polysaccharide of claim 9 wherein said low molecular weight polysaccharide residue is derived from degraded galactomannan gum.

13. A polysaccharide of claim 12 wherein said degraded galactomannan gum comprises guar, tara, fenugreek, or locust bean gum.

14. A process for preparing a polysaccharide comprising at least one oxime linkage, said process comprising contacting a first saccharide with a second saccharide in the presence of galactose oxidase, wherein each of said saccharides comprises at least one —$ONH_2$ functionality and at least one —$CH_2OH$ functionality oxidizable by said galactose oxidase.

15. A process of claim 14 wherein said saccharides are derived from galactose.

16. A process of claim 14 wherein said saccharides are derived from lactose, melibiose, or galactosyl arabinose.

17. A process of claim 14 wherein said saccharides are derived from degraded galactomannan gum.

18. A process of claim 17 wherein said degraded galactomannan gum comprises guar, tara, fenugreek, or locust bean gum.

19. A process of claim 14 wherein said saccharides comprise terminal or pendant moieties capable of being oxidized by said galactose oxidase.

20. A process of claim 14 wherein said polysaccharide has a weight average molecular weight of at least about 1000 daltons.

21. A process of claim 14 wherein said polysaccharide has a weight average molecular weight of at least about 4000 daltons.

22. A polysaccharide comprising at least two oxime linkages prepared by the process of claim 14.

23. A process of preparing a polysaccharide comprising at least one oxime linkage, said process comprising contacting a first saccharide with a second saccharide, wherein each of said saccharides comprises at least one —$ONH_2$ functionality and at least one precursor to a —CHO functionality, and converting said precursor to said —CHO functionality.

24. A process of claim 23 wherein said precursor comprises a —$CH_2OH$ functionality which is oxidized to a —CHO functionality.

25. A process of claim 24 wherein said oxidation comprises enzymatic oxidation.

26. A polysaccharide comprising at least two oxime linkages prepared by the process of claim 23.

27. A process of preparing a polysaccharide comprising at least one oxime linkage, said process comprising contacting a first saccharide with a second saccharide, wherein each of said saccharides comprises at least one —CHO functionality and at least one —$ONH_2$ functionality.

28. A polysaccharide comprising at least two oxime linkages prepared by the process of claim 27.

29. A polymer composition comprising the polysaccharide of claim 1 and paper pulp.

30. A flucculant comprising the polysaccharide of claim 1.

31. A retention aid for paper pulp comprising the polysaccharide of claim 1.

32. A personal care formulation comprising the polysaccharide of claim 1.

33. A polysaccharide comprising at least two oxime linkages.

34. A polysaccharide of claim 33 having a weight average molecular weight of at least about 1000 daltons.

35. A polysaccharide of claim 34 having a weight molecular weight of at least about 4000 daltons.

36. A polysaccharide of claim 33 which comprises a plurality of saccharide residues selected from the group consisting of monosaccharide, disaccharide, trisaccharide, and low molecular weight polysaccharide residues.

37. A polysaccharide of claim 36 wherein said monosaccharide residue is derived from galactose.

38. A polysaccharide of claim 36 wherein said disaccharide residue is derived from lactose, melibiose, or galactosyl arabinose.

39. A polysaccharide of claim 36 wherein said low molecular weight polysaccharide residue is derived from degraded galactomannan gum.

40. A polysaccharide of claim 39 wherein said degraded galactomannan gum comprises guar, tara, fenugreek, or locust bean gum.

* * * * *